United States Patent
Wang et al.

(10) Patent No.: US 10,914,565 B2
(45) Date of Patent: Feb. 9, 2021

(54) BLADE INSPECTION DEVICE AND METHOD AND PRINTING MODIFICATION DEVICE

(71) Applicants: Ordos Yuansheng Optoelectronics Co., Ltd., Inner Mongolia (CN); BOE TECHNOLOGY GROUP CO., LTD., Beijing (CN)

(72) Inventors: Lina Wang, Beijing (CN); Dawei Ma, Beijing (CN); Chunchieh Huang, Beijing (CN); Zifeng Wang, Beijing (CN)

(73) Assignees: ORDOS YUANSHENG OPTOELECTRONICS CO., LTD., Inner Monogolia (CN); BOE TECHNOLOGY GROUP CO., LTD., Beijing (CN)

( * ) Notice: Subject to any disclaimer, the term of this patent is extended or adjusted under 35 U.S.C. 154(b) by 32 days.

(21) Appl. No.: 16/332,340

(22) PCT Filed: Jun. 27, 2018

(86) PCT No.: PCT/CN2018/093084
§ 371 (c)(1),
(2) Date: Mar. 11, 2019

(87) PCT Pub. No.: WO2019/041998
PCT Pub. Date: Mar. 7, 2019

(65) Prior Publication Data
US 2020/0182600 A1    Jun. 11, 2020

(30) Foreign Application Priority Data
Aug. 31, 2017  (CN) .......................... 2017 1 0772838

(51) Int. Cl.
*B41F 15/46* (2006.01)
*G01B 5/06* (2006.01)
(Continued)

(52) U.S. Cl.
CPC .............. *G01B 5/068* (2013.01); *B41F 15/44* (2013.01); *B41F 33/0027* (2013.01); *G08B 7/06* (2013.01); *G08B 21/182* (2013.01)

(58) Field of Classification Search
CPC ...... G01B 5/068; B41F 15/44; B41F 33/0027; B41F 15/46; G08B 7/06; G08B 21/182; H05K 3/1216; B23K 1/0016
See application file for complete search history.

(56) References Cited

U.S. PATENT DOCUMENTS 4,414,894 A * 11/1983 Bailly .................. H05K 3/1216
                                                    101/123
6,131,510 A * 10/2000 Gasquez ................. B41F 15/42
                                                    101/114
(Continued)

FOREIGN PATENT DOCUMENTS

CN    107389877 A    11/2017
DE    15 48 305 A1    2/1970
(Continued)

OTHER PUBLICATIONS

International Search Report and Written Opinion dated Aug. 21, 2018, from application No. PCT/CN2018/093084.

*Primary Examiner* — An T Nguyen
(74) *Attorney, Agent, or Firm* — Thomas|Horstemeyer, LLP (57) ABSTRACT

The present disclosure provides a blade inspection device, a method and a printing modification device, and belongs to the technical field of screen printing. The blade inspection device includes a telescopic component, a driving component and a parameter obtaining module. The driving com- (Continued)

ponent is configured to drive the telescopic component to move in a direction parallel to the line where the blade is located. The parameter obtaining module is configured to obtain a first parameter to inspect the blade according to the first parameter. The first parameter is related to a displacement of the first end of the telescopic component in a direction perpendicular to the line where the blade is located.

20 Claims, 3 Drawing Sheets

(51) Int. Cl.
*B41F 15/44* (2006.01)
*B41F 33/00* (2006.01)
*G08B 7/06* (2006.01)
*G08B 21/18* (2006.01)

(56) References Cited

U.S. PATENT DOCUMENTS

| | | | | |
|---|---|---|---|---|
| 2009/0255425 | A1* | 10/2009 | Itoh | H05K 3/1233 |
| | | | | 101/126 |
| 2013/0192480 | A1* | 8/2013 | Abe | B41F 15/26 |
| | | | | 101/123 |
| 2014/0318393 | A1* | 10/2014 | Kobayashi | B41F 15/0881 |
| | | | | 101/123 |
| 2015/0336377 | A1* | 11/2015 | Sueyasu | B41F 15/40 |
| | | | | 101/123 |
| 2017/0232726 | A1* | 8/2017 | Bennett | B41F 15/44 |
| | | | | 101/123 |

FOREIGN PATENT DOCUMENTS

| | | |
|---|---|---|
| GB | 1 103 428 A | 2/1968 |
| JP | H-11-183106 A | 7/1999 |

* cited by examiner

BLADE INSPECTION DEVICE AND METHOD AND PRINTING MODIFICATION DEVICE

CROSS-REFERENCE TO RELATED APPLICATIONS

The present application is based upon International Application No. PCT/CN2018/093084, filed on Jun. 27, 2018, which claims the priority to the Chinese Patent Application No. 201710772838.6, filed on Aug. 31, 2017, the entire contents of which are hereby incorporated as a part of the present application by reference.

TECHNICAL FIELD

The present disclosure belongs to the field of screen printing technology, and in particular, to a blade inspection device, a blade inspection method, and a printing modification device using the blade inspection.

BACKGROUND

Screen printing has a wide range of applications, for example, it can be used in display panel packaging processes. Taking an OLED (Organic Light-Emitting Diode) display panel as an example, as a new type of flat panel display, it has received more and more attention and become the next generation display technology that may replace liquid crystal display due to the characteristics of active illumination, high luminance, wide viewing angle, fast response, low power consumption, flexibility and the like.

Current OLED devices have organic layer materials that are extremely sensitive to moisture and oxygen, which greatly reduces the lifetime of OLED devices. In order to solve this problem, in the prior art, various materials are mainly used to isolate the organic layer material of the OLED from the outside, so that the sealing property satisfies the demand. A common sealing method is: filling an adhesive such as a glass frit in a sealing area of a package cover, aligning an array substrate with the package cover, and then moving a laser beam to heat and melt the adhesive, so that the melted adhesive forms a sealed package connection between the package cover and the array substrate.

SUMMARY

According to an aspect of the present disclosure, there is provided a blade inspection device. The blade inspection device includes a telescopic component. A first end of the telescopic component is in contact with a blade of a printing squeegee, and a second end of the telescopic component is located at a motion interval parallel to a line where the blade is located and movable along the motion interval. A connecting line between the first end of the telescopic component and the second end of the telescopic component is perpendicular to the line where the blade is located. The blade inspection device includes a driving component configured to drive the telescopic component to move in a direction parallel to the line where the blade is located. The blade inspection device includes a parameter obtaining module configured to obtain a first parameter so as to inspect the blade according to the first parameter. The first parameter is related to a displacement of the first end of the telescopic component in a direction perpendicular to the line where the blade is located.

In an exemplary arrangement of the present disclosure, the telescopic component includes a spring component. A first end of the spring component is in contact with the blade of the printing squeegee, and a second end of the spring component is located at the motion interval parallel to the line where the blade is located and is movable along the motion interval. The spring component is in a stretched state.

The parameter obtaining module includes a tension measurement component coupled to the second end of the spring component to obtain a tension value of the spring component as the first parameter.

In an exemplary arrangement of the present disclosure, the telescopic component further includes a spring fixing component. The spring fixing component is sleeved on a periphery of the spring component to ensure that the spring component is perpendicular to the line where the blade is located while moving in the direction parallel to the line where the blade is located.

In an exemplary arrangement of the present disclosure, the telescopic component includes an extension component. A first end of the extension component is in contact with the blade of the printing squeegee, and a second end of the extension component is located at the motion interval parallel to the line where the blade is located and is movable along the motion interval. The extension is a rigid body.

The parameter obtaining module includes a displacement sensor. The displacement sensor is configured to obtain the displacement of the first end of the extension component in the direction perpendicular to the line where the blade is located as the first parameter.

In an exemplary arrangement of the present disclosure, the telescopic component further includes a driving unit. The driving unit is coupled to the second end of the extension component to drive movement of the extension component in the direction perpendicular to the line where the blade is located to maintain the first end of the extension component in contact with the blade of the printing squeegee.

In an exemplary arrangement of the present disclosure, the displacement sensor includes a displacement conversion circuit configured to generate an electrical signal related to the displacement of the first end of the extension component in the direction perpendicular to the line where the blade is located. The displacement sensor includes a signal amplification circuit, configured to perform amplification processing on the electrical signal. The displacement sensor includes an analog-to-digital conversion circuit. The analog-to-digital conversion circuit is configured to convert the amplified electrical signal into a digital signal, and calculate the displacement of the first end of the extension component in the direction perpendicular to the line where the blade is located according to the digital signal.

In an exemplary arrangement of the present disclosure, the displacement sensor includes a first microprocessor, and the first microprocessor is configured to generate an electrical signal related to the displacement of the first end of the extension component in the direction perpendicular to the line where the blade is located. The first microprocessor is configured to perform amplification processing on the electrical signal. The first microprocessor is configured to convert the amplified electrical signal into a digital signal, and calculate the displacement of the first end of the extension component in the direction perpendicular to the line where the blade is located according to the digital signal.

In an exemplary arrangement of the present disclosure, the blade inspection device further includes a calculation circuit, configured to calculate a difference between the first parameter and a preset parameter. The blade inspection device includes an alarm unit configured to perform an alarm prompt when the difference is greater than a preset threshold.

In an exemplary arrangement of the present disclosure, the displacement sensor further include a second microprocessor. The second microprocessor is configured to calculate a difference between the first parameter and a preset parameter. The second microprocessor is configured to perform an alarm prompt when the difference is greater than a preset threshold.

In an exemplary arrangement of the present disclosure, the alarm unit includes performing the alarm prompt by way of sound and/or light.

According to an aspect of the present disclosure, there is provided a blade inspection method applied to anyone of the blade inspection devices described above. The blade inspection method includes driving the telescopic component to move in a direction parallel to a line where the blade is located. The blade inspection method includes obtaining the first parameter, and inspecting the blade according to the first parameter, the first parameter being related to a displacement of a first end of the telescopic component in a direction perpendicular to the line where the blade is located.

In an exemplary arrangement of the present disclosure, the blade inspection method further includes calculating a difference between the first parameter and a preset parameter, and performing an alarm prompt when the difference is greater than a preset threshold.

According to an aspect of the present disclosure, there is provided a printing modification device. The printing modification device includes a printing squeegee and anyone of the blade inspection devices described above.

It is understood that the above general description and the following detailed description are merely exemplary and explanatory and should not be construed as limiting of the present disclosure.

BRIEF DESCRIPTION OF THE DRAWINGS

The accompanying drawings, which are incorporated in the specification and constitute a part of the specification, show exemplary arrangements of the present disclosure. The drawings along with the specification explain the principles of the present disclosure. It is apparent that the drawings in the following description show only some of the arrangements of the present disclosure, and other drawings may be obtained by those skilled in the art without departing from the drawings described herein.

DETAILED DESCRIPTION

Example arrangements will now be described more fully with reference to the accompanying drawings. However, the arrangements can be implemented in a variety of forms and should not be construed as being limited to the examples set forth herein; rather, these arrangements are provided so that this disclosure will be more complete so as to convey the idea of the exemplary arrangements to those skilled in this art. The same reference numerals in the drawings denote the same or similar parts, and the repeated description thereof will be omitted.

Although the relative terms such as "above" and "below" are used in the specification to describe the relative relationship of one component to another component shown in the figure, these terms are used in this specification for convenience only, for example, according to the direction of the example described in the accompanying drawings. It will be understood that if the device shown in the figure is flipped upside down, the component described "above" will become the component "below". Other relative terms, such as "high", "low", "top", "bottom", "left", "right", etc., have similar meanings. When one structure is "on" another structure, it is possible that the one structure is integrally formed on the another structure, or that the one structure is "directly" disposed on the another structure, or that the one structure is "indirectly" disposed on the another structures through another structure.

The terms "one", "an", and "the" are used to represent the presence of one or more elements/components, etc.; the terms "including" and "having" are used to represent including in an opening manner and represent that there may be additional elements/components/etc. in addition to the listed elements/components/etc.

Figure 1:
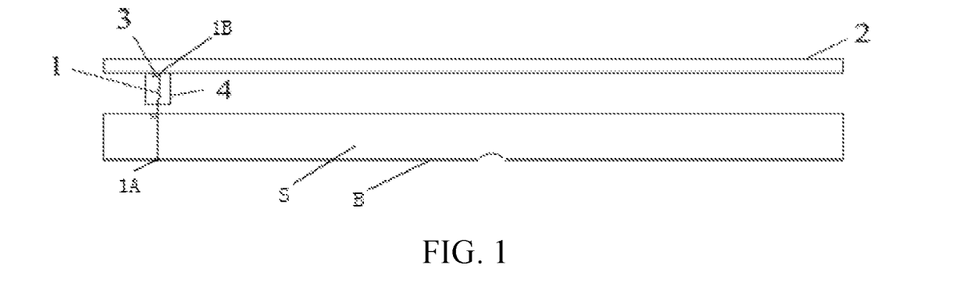
FIG. 1 is a schematic structural view showing a blade inspection device in an exemplary arrangement of the present disclosure.
Figure 2:
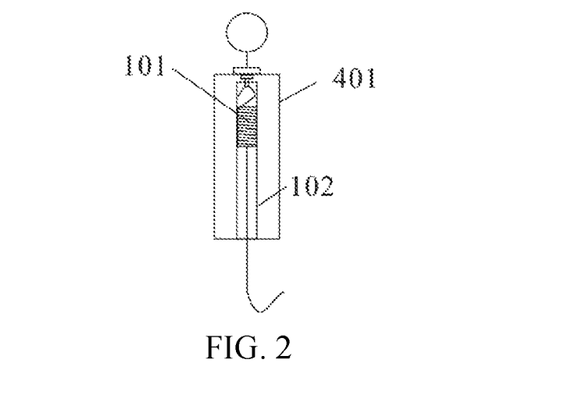
FIG. 2 is a schematic structural view showing a spring component as a telescopic component in an exemplary arrangement of the present disclosure.
Figure 3:
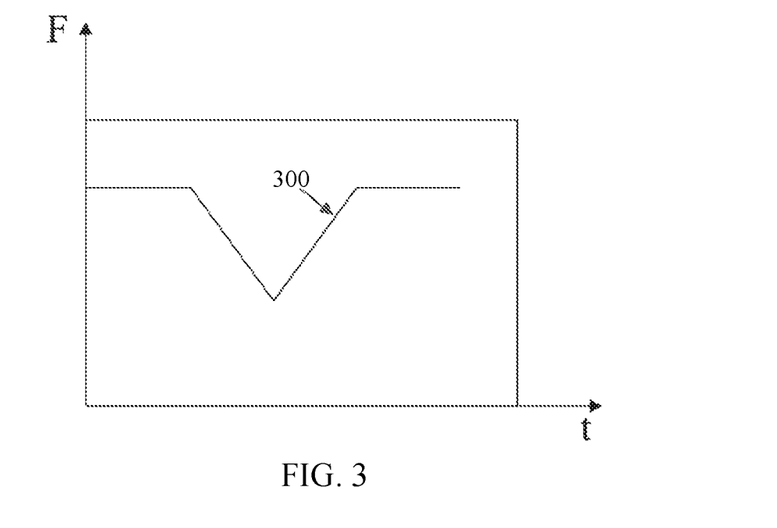
FIG. 3 illustrates a graph of tension experienced by a spring component as a function of displacement in an exemplary arrangement of the present disclosure.
Figure 4:
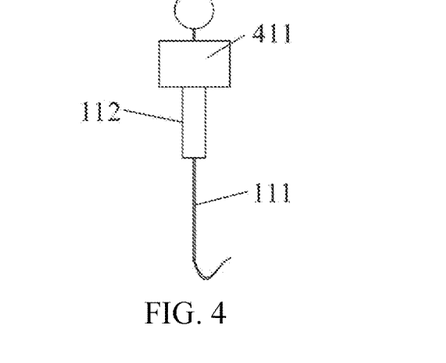
FIG. 4 is a schematic structural view showing another telescopic component in an exemplary arrangement of the present disclosure.
Figure 5:
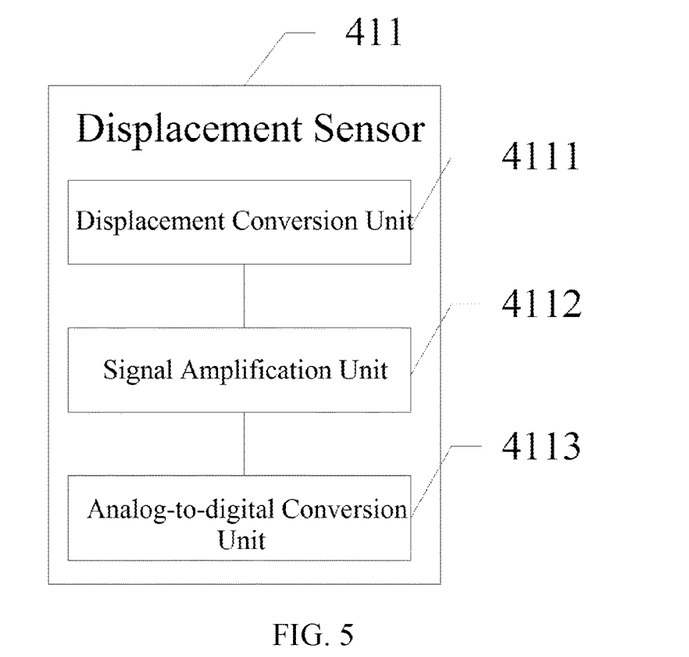
FIG. 5 illustrates a block diagram of a sensor in an exemplary arrangement of the present disclosure.
Figure 6:
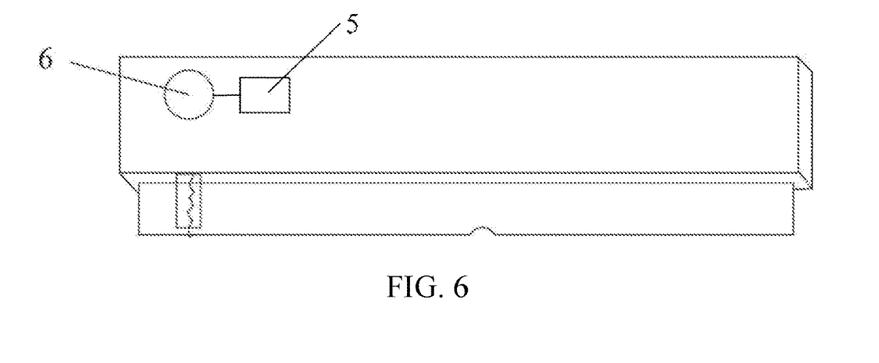
FIG. 6 is a schematic structural view showing a printing squeegee device with an alarm in an exemplary arrangement of the present disclosure.
Figure 7:
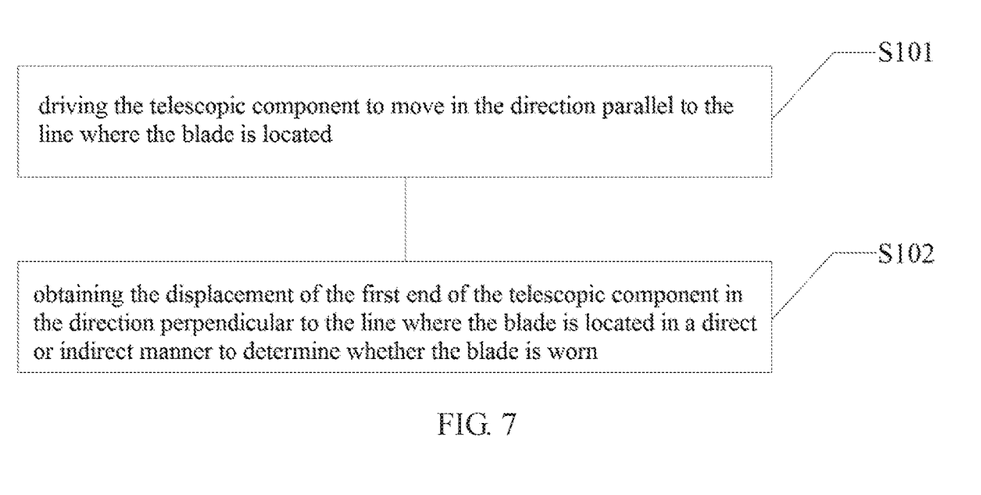
FIG. 7 illustrates a flow chart of a blade inspection method in an exemplary arrangement of the present disclosure.

FIG. 1 is a schematic structural view showing a blade inspection device in an exemplary arrangement of the present disclosure; FIG. 2 is a schematic structural view showing a spring component as a telescopic component in an exemplary arrangement of the present disclosure; FIG. 3 illustrates a graph of tension experienced by a spring component as a function of displacement in an exemplary arrangement of the present disclosure; FIG. 4 is a schematic structural view showing another telescopic component in an exemplary arrangement of the present disclosure; FIG. 5 illustrates a block diagram of a sensor in an exemplary arrangement of the present disclosure; FIG. 6 is a schematic structural view showing a printing squeegee device with an alarm in an exemplary arrangement of the present disclosure; FIG. 7 illustrates a flow chart of a blade inspection method in an exemplary arrangement of the present disclosure.

The present exemplary arrangement provides a schematic structural view of a blade inspection device. Referring to FIG. 1, the blade inspection device may include a telescopic component 1, a motion interval 2 parallel to a line where the blade B is located, a driving component 3, and a parameter obtaining module 4. A first end 1A of the telescopic component 1 is in contact with the blade, a second end 1B of the telescopic component is located at the motion interval 2 and is movable along the motion interval 2, and a connecting line between the first end of the telescopic component 1 and the second end of the telescopic component 1 is perpendicular to the line where the blade is located. The parameter obtaining module 4 is configured to obtain a first parameter.

In the present arrangement, the motion interval 2 may be a recess that accommodates the second end of the telescopic component 1, so that the second end is movable within a range defined by the motion interval 2. The present disclosure is not limited thereto, and the motion interval 2 may also be other structures for accommodating, defining or guiding the telescopic component 1. The driving component 3 can provide mechanical or electromagnetic force, so that the telescopic component moves in a direction parallel to the blade B within a range defined by the motion interval 2

The blade inspection device provided by the present exemplary arrangement includes a telescopic component, a driving component and a parameter obtaining module. The driving component is configured to drive the telescopic component to move in a direction parallel to the line where the blade is located; the parameter obtaining module is configured to obtain a displacement of the first end of the telescopic component in a direction perpendicular to the line where the blade is located. It can be quickly inspected whether there are defects of the printing squeegee by the displacement value, which can overcome the shortcomings of slow speed and the difficulty of distinguishing the depth of the notch when the human eye observes the defect of the blade of the printing squeegee, thus effectively controlling the process, so that the printed surface of the adhesive is not caused to have different topographies by the defect of the printing squeegee in the products produced in each batch, thus meeting production needs.

For example, the blade inspection device can be applied to a printing squeegee used when the OLED device is packaging through glass cement. For example, the printing squeegee is dismountably mounted on a cross beam of a printing machine. The cross beam of the printing machine can be a cuboid structure, of which the lower end is provided with a recess or a clip, and the like, for fixing the printing squeegee and realizing the dismountable function of the printing squeegee. Of course, the structure of the cross beam of the printing machine can also be other structures, such as a hand-held hollow structure with a recess, two splints that can be spliced together, etc.; that is, as long as the structure can fix the printing squeegee and facilitate the disassembly of the printing squeegee, it will fall in the protection scope of the present disclosure, which is not limited herein.

A parallel rod parallel to the line where the blade B of the printing squeegee S is located can be fixedly mounted on the cross beam of the printing machine, which can be used as the motion interval 2. The second end of the telescopic component 1 can be fixed on the parallel rod by the way of magnetically attracting, sleeving, stucking, hooking, etc. and is moveable along the parallel rod, that is, the connection between the second end of the telescopic component and the parallel rod can be implemented in various conventional manners, as long as the second end can be moveable along the parallel rod and fixed on the parallel rod, which is not limited herein. The first end of the telescopic component 1 can be contacted with the blade of the printing squeegee by a hook or the like. Of course, the first end of the telescopic component 1 can also be contacted with the blade of the printing squeegee by other means, such as magnetic mode, as long as it does not affect the movement of the first end of the telescopic component along the blade.

The driving component can be mounted on the printing machine to drive the telescopic component to move in a direction parallel to the line where the blade is located. The driving mode can be electric driving or mechanical driving.

In order to ensure that the connecting line between the first end and the second end of the driving component is always perpendicular to the line where the blade is located when the telescopic component is moving along the blade. Multiple driving blocks can be mounted on the parallel rod and on the back of the printing blade, and the electric driving is used to make the multiple driving blocks move at the same speed, so that the connecting line between the first end and the second end of the telescopic component is always perpendicular to the line where the blade is located when the telescopic component is moving along the blade.

The telescopic component 1 can be an elastic component, such as a spring component, and the telescopic component 1 can also be a rigid component that has an extension component and can move along a direction perpendicular to the line where the blade is located, for example, a structure of a steel tube sleeving on a steel rod.

Taking an elastic component as an example of the telescopic component, as shown in FIG. 2, the telescopic component 1 includes a spring component 101. The first end of the spring component 101 is in contact with the blade of the printing squeegee, and the second end of the spring component 101 is located at a motion interval parallel to the line where the blade is located and is movable along the motion interval. The spring component 101 is perpendicular to the line where the blade is located. The parameter obtaining module 4 includes a tension measurement component 401 located at the second end of the spring component 101 for measuring the tension of the first end of the spring component 101. The telescopic component 1 further includes a spring fixing component 102 for maintaining the spring component 101 perpendicular to the line where the blade is located without deflection during lateral movement of the spring component 101.

For example, the spring component may be a spring, the first end of the spring may have a hook shape, hooked on the blade of the printing squeegee, and the second end may have a ring, sleeved on the parallel rod. The spring is always in a stretched state, the second end of the spring is equipped with a tension measurement device which is used to measure the tension of the first end of the spring and can display the tension value. A fixing component which is perpendicular to the line where the blade is located can be mounted on the telescopic component. The fixing component is of a rigid material, such as a steel cover, for fixing the spring to be perpendicular to the line where the blade is located when moving along the blade. When the spring is driven by the driving component to move along the direction parallel to the line where the blade of the printing squeegee is located, the curve of the tension varying according to time can be drawn by the computer value, and it is determined, according to the curve, whether there is a defect on the blade of the printing squeegee and whether the printing squeegee needs to be replaced. Referring to FIG. 3, shown in a curve 300 of the tension varying with time when there is a defect on the blade of the printing squeegee.

Taking a rigid extension component as an example of the telescopic component, as shown in FIG. 4, the telescopic component 1 may also include an extension component 111. A first end of the extension component is in contact with the blade of the printing squeegee, and a second end of the extension component is located at a motion interval parallel to the line where the blade is located and is movable along the motion interval, and the extension component 111 is a rigid body. The parameter obtaining module includes a displacement sensor 411, configured to obtain the displacement of the first end of the extension component 111 in a direction perpendicular to the line where the blade is located.

Further, the telescopic component 1 further includes a driving unit 112, coupled to the second end of the extension component 111 to drive the extension component 111 to move in a direction perpendicular to the line where the blade is located to maintain the first end of the extension component 111 in contact with the blade of the printing squeegee.

For example, the extension component is a rigid rod, such as a metal rod, a first end of the metal rod is in contact with the blade of the printing squeegee through a metal hook, and the metal rod can have magnetism to attach the metal rod on the printing squeegee, so that the metal rod and the printing squeegee fits well. The driving unit can be connected to the second end of the metal rod by sleeving, and make the metal rod move along the direction perpendicular to the line where the blade is located. The driving unit can be fixed on the horizontal rod by magnetic attraction or stucking. When the driving unit and the metal rod move along the direction parallel to the line where the blade is located simultaneously, the displacement sensor obtains the displacement of the first end of the metal rod in a direction perpendicular to the line where the blade is located.

Further, as shown in FIG. 5, the displacement sensor 411 includes a displacement conversion unit 4111, a signal amplification unit 4112, and an analog-to-digital conversion unit 4113. The displacement conversion unit 4111 is configured to generate an electrical signal related to a displacement of the first end of the extension component in the direction perpendicular to the line where the blade is located; the signal amplifying unit 4112 is configured to perform amplification processing on the electrical signal; and the analog-to-digital conversion unit 4113 is configured to convert the amplified electrical signal into a digital signal, and calculate a displacement of the first end of the extension component in the direction perpendicular to the line where the blade is located according to the digital signal.

For example, the displacement sensor may include a displacement conversion unit, a signal amplification unit, and an analog-to-digital conversion unit. When the driving component drives the metal rod to move in a direction parallel to the line where the blade is located, first, the displacement conversion unit generates an electrical signal related to a displacement of the first end of the metal rod in the direction perpendicular to the line where the blade is located; then, the signal amplifying unit performs amplification processing on the electrical signal; finally, the analog-to-digital conversion unit converts the amplified electrical signal into a digital signal, and calculates a displacement of the first end of the metal rod in the direction perpendicular to the line where the blade is located according to the digital signal.

In the present arrangement, the displacement conversion unit 4111, the signal amplification unit 4112, and the analog-to-digital conversion unit 4113 may be implemented by a corresponding displacement conversion circuit, signal amplification circuit, or digital-to-analog conversion circuit. However, the present disclosure is not limited thereto, and the displacement converting unit 4111, the signal amplifying unit 4112, and the analog-to-digital converting unit 4113 may also be implemented by a first microprocessor configured to perform a corresponding operation. In one arrangement of the present disclosure, the first microprocessor may represent a digital processor unit capable of performing digital logic operations. For example, the first microprocessor may be configured to execute computer readable code stored in the memory, thus performing the corresponding operation.

The parameter obtaining module 4 can obtain the displacement of the first end of the telescopic component in a direction perpendicular to the line where the blade is located by direct or indirect manner. The indirect obtaining method may be such that when the deformation is the elastic deformation, the displacement value is converted into a tension value by a spring tension meter, and the position where the defect of the blade is located is found by the change of the tension value. The direct obtaining method may be such that when the deformation is the displacement of the relative movement of the two components, the displacement value is directly measured, and the displacement value is further converted into a digital signal by the displacement sensor, and the displacement of the first end of the telescopic component in a direction perpendicular to the line where the blade is located is calculated based on the digital signal.

Further, the blade inspection device may further include a calculation unit 5 and an alarm unit 6; the calculation unit 5 is configured to calculate a difference between the displacement value or the tension value and the preset displacement value or tension value. When the difference is greater than the displacement threshold or the tension threshold, the alarm unit 6 issues an alarm signal.

For example, as shown in FIG. 6, the alarm device is disposed on the cross beam of the printing machine. Taking a spring component as an example of the telescopic component, when the calculated difference is greater than the tensile threshold, the difference is an absolute value of the difference between the tension value of the first end of the spring and the preset tension value of the calculation unit, the alarm unit issues an alarm signal, which may be an audio signal or an optical signal, or a combination of the two, and the specific alarm mode is not limited herein. The preset tension value of the calculation unit may be the tension value of the first end of the spring when the blades of printing squeegees in a same batch are sound.

In this arrangement, the calculation unit 5 can be implemented by a corresponding calculation circuit. However, the present disclosure is not limited thereto, and the calculation unit 5 may also be implemented by a second microprocessor configured to perform a corresponding operation. In one arrangement of the present disclosure, the second microprocessor may represent a digital processor unit capable of performing digital logic operations. For example, the second microprocessor may be configured to execute computer readable code stored in the memory, thus performing the corresponding operation.

The present exemplary arrangement provides a flowchart of a blade inspection method. Referring to FIG. 7, the blade inspection method may include the following blocks.

In block S101, the telescopic component is driven to move in a direction parallel to the line where the blade is located.

In block S102, the first parameter is obtained, and the blade is inspected according to the first parameter. The first parameter is related to a displacement of a first end of the telescopic component in a direction perpendicular to a line where the blade is located.

Referring again to block S101 and in greater detail, the telescopic component moves along a direction parallel to the line where the blade is located under the driving of the driving component. For example, the spring component or the rigid extension component moves along a direction parallel to the line where the blade is located under the electric driving or mechanical driving of the driving component.

Referring again to block S102 and in greater detail, the displacement of the first end of the telescopic component in a direction perpendicular to the line where the blade is located is obtained by direct or indirect manner, thus determining whether the blade is worn.

Taking a spring as an example of the telescopic component, the spring moves along a direction parallel to the line where the blade is located under the driving of the driving component. The driving can be an electric driving, such as a driving button. When the driving button is pressed, the spring begins to move along a direction parallel to the line where the blade is located. The driving can also be mechanical driving. For example, the spring is dragged by a dragging device to move along a direction parallel to the line where the blade is located. The spring tension meter measures the tension value of the first end of the spring in a direction perpendicular to the line where the blade is located, and determines whether there is a defect on the blade of the printing squeegee by the change of the tension value.

Taking a rigid extension component as an example of the telescopic component, the rigid extension component moves along a direction parallel to the line where the blade is located under the driving of the driving component, and moves along a direction perpendicular to the line where the blade is located under the driving of the driving unit. The displacement of the first end of the rigid extension component in the vertical direction is measured by a displacement measurement meter to determine whether there is a defect on the blade of the printing squeegee. Further, the displacement of the first end of the rigid extension component in the direction perpendicular to the line where the blade is located is converted into an electric signal by the displacement sensor, and the electric signal is amplified. The amplified electrical signal is converted into a digital signal, and the displacement of the first end of the rigid extension component in the direction perpendicular to the line where the blade is located is calculated according to the digital signal, thus determining whether there is a defect on the blade of the printing squeegee.

The blade inspection device mentioned in the above exemplary arrangement is suitable for the inspection of the blade of the printing squeegee in all the printing modification process.

The verticals mentioned in the above exemplary arrangements are not geometrically vertical, and the vertical in the printing process may have a certain range of deviations at right angles, and the right angle and right angle deviation ranges are within the protection scope of the present disclosure.

The present disclosure provides a blade inspection device, a blade inspection method, and a print modification device using the blade inspection. The blade inspection device provided by the present disclosure includes a telescopic component, a driving component and a parameter obtaining module. The driving component is configured to drive the telescopic component to move in a direction parallel to the line where the blade is located; the parameter obtaining module is configured to obtain a displacement of the first end of the telescopic component in a direction perpendicular to the line where the blade is located. It can be quickly inspected whether there are defects on the blade of the printing squeegee by the displacement value, which can overcome the shortcomings of slow speed and the difficulty of distinguishing the depth of the notch when the human eye observes the defect of the blade of the printing squeegee, thus effectively controlling the process, so that the printed surface of the adhesive is not caused to have different topographies by the defect of the printing squeegee in the products produced in each batch, thus meeting production needs It should be understood that the present disclosure does not limit its application to the detailed structure and arrangement of the components presented in the specification. The present disclosure can have other arrangements, and can be implemented and performed in various manners. The foregoing variations and modifications are intended to fall within the scope of the present disclosure. It is to be understood that the present disclosure disclosed and defined by the specification extends to all alternative combinations of two or more individual features that are mentioned or apparent in the context and/or drawings. All of these different combinations constitute a number of alternative aspects of the present disclosure. The arrangements described in the specification are illustrative of the best mode for carrying out the present disclosure and will enable those skilled in the art to utilize the present disclosure.

What is claimed is:

1. A blade inspection device, comprising:
   a telescopic component, having a first end in contact with a blade of a printing squeegee, and a second end located at a motion interval parallel to a line where the blade is located and being movable along the motion interval, wherein a connecting line between the first end and the second end of the telescopic component is perpendicular to the line where the blade is located;
   a driving component, configured to drive the telescopic component to move in a direction parallel to the line where the blade is located; and
   a parameter obtaining module, configured to obtain a first parameter, so as to inspect the blade according to the first parameter, wherein the first parameter is related to a displacement of the first end of the telescopic component in a direction perpendicular to the line where the blade is located.

2. The blade inspection device according to claim 1, wherein the telescopic component comprises a spring component that has a first end in contact with the blade of the printing squeegee, and a second end located at the motion interval parallel to the line where the blade is located and movable along the motion interval, and the spring component is in a stretched state; and
   the parameter obtaining module comprises a tension measurement component coupled to the second end of the spring component to obtain a tension value of the spring component as the first parameter.

3. The blade inspection device according to claim 2, wherein the telescopic component further comprises:
   a spring fixing component, sleeved on a periphery of the spring component to ensure that the spring component is perpendicular to the line where the blade is located when moving in the direction parallel to the line where the blade is located.

4. The blade inspection device according to claim 1, wherein the telescopic component comprises an extension component that has a first end in contact with the blade of the printing squeegee, and a second end located at the motion interval parallel to the line where the blade is located and movable along the motion interval, and the extension component is a rigid body; and
   the parameter obtaining module comprises a displacement sensor, configured to obtain a displacement of the first end of the extension component in the direction perpendicular to the line where the blade is located as the first parameter.

5. The blade inspection device according to claim 4, wherein the telescopic component further comprises:
a driving unit, coupled to the second end of the extension component to drive the extension component to move in the direction perpendicular to the line where the blade is located, so that the first end of the extension component is in contact with the blade of the printing squeegee.

6. The blade inspection device according to claim 4, wherein the displacement sensor comprises:
a displacement conversion circuit, configured to generate an electrical signal related to the displacement of the first end of the extension component in the direction perpendicular to the line where the blade is located;
a signal amplification circuit, configured to perform amplification processing on the electrical signal; and
an analog-to-digital conversion circuit, configured to convert the electrical signal amplified into a digital signal, and calculate the displacement of the first end of the extension component in the direction perpendicular to the line where the blade is located according to the digital signal.

7. The blade inspection device according to claim 4, wherein the displacement sensor comprises a first microprocessor, and the first microprocessor is configured to:
generate an electrical signal related to the displacement of the first end of the extension component in the direction perpendicular to the line where the blade is located;
perform amplification processing on the electrical signal; and
convert the electrical signal amplified into a digital signal, and calculate the displacement of the first end of the extension component in the direction perpendicular to the line where the blade is located according to the digital signal.

8. The blade inspection device according to claim 1, further comprising:
a calculation circuit, configured to calculate a difference between the first parameter and a reference parameter;
an alarm unit, configured to perform an alarm prompt when the difference is greater than a threshold.

9. The blade inspection device according to claim 1, further comprising a microprocessor, wherein the microprocessor is configured to:
calculate a difference between the first parameter and a reference parameter; and
perform an alarm prompt when the difference is greater than a threshold.

10. A blade inspection device according to claim 8, wherein the alarm unit performs the alarm prompt by way of at least one of sound and light.

11. A blade inspection method applied to a blade inspection device, comprising:
providing the blade inspection device, the blade inspection device comprising:
a telescopic component having a first end in contact with a blade of a printing squeegee, and a second end located at a motion interval parallel to a line where the blade is located and being movable along the motion interval, wherein a connecting line between the first end and the second end of the telescopic component is perpendicular to a line where the blade is located;

a driving component configured to drive the telescopic component to move in a direction parallel to the line where the blade is located; and
a parameter obtaining module configured to obtain a first parameter so as to inspect the blade according to the first parameter, wherein the first parameter is related to a displacement of the first end of the telescopic component in a direction perpendicular to the line where the blade is located;
driving the telescopic component to move in the direction parallel to the line where the blade is located; and
obtaining the first parameter, and inspecting the blade according to the first parameter, wherein the first parameter is related to the displacement of the first end of the telescopic component in the direction perpendicular to the line where the blade is located.

12. The blade inspection method according to claim 11, further comprising:
calculating a difference between the first parameter and a reference parameter; and
performing an alarm prompt when the difference is greater than a threshold.

13. A printing modification device, comprising a printing squeegee and a blade inspection device, wherein the blade inspection device comprises:
a telescopic component, having a first end in contact with a blade of the printing squeegee, and a second end located at a movement interval parallel to a line where the blade is located and being movable along a motion interval, wherein a connecting line between the first end and the second end of the telescopic component is perpendicular to the line where the blade is located;
a driving component, configured to drive the telescopic component to move in a direction parallel to the line where the blade is located; and
a parameter obtaining module, configured to obtain a first parameter, so as to inspect the blade according to the first parameter, wherein the first parameter is related to a displacement of the first end of the telescopic component in a direction perpendicular to the line where the blade is located.

14. The printing modification device according to claim 13, wherein the telescopic component comprises a spring component, which has a first end in contact with the blade of the printing squeegee, and a second end being located at the motion interval parallel to the line where the blade is located and being movable along the motion interval, and the spring component is in a stretched state; and
the parameter obtaining module comprises a tension measurement component coupled to the second end of the spring component to obtain a tension value of the spring component as the first parameter.

15. The printing modification device according to claim 14, wherein the telescopic component further comprises:
a spring fixing component, sleeved on a periphery of the spring component to ensure that the spring component is perpendicular to the line where the blade is located when moving in the direction parallel to the line where the blade is located.

16. The printing modification device according to claim 13, wherein the telescopic component comprises an extension component, which has a first end in contact with the blade of the printing squeegee, and a second end being located at the motion interval parallel to the line where the blade is located and being movable along the motion interval, and the extension component is a rigid body; and the parameter obtaining module comprises a displacement sensor, configured to obtain a displacement of the first end of the extension component in the direction perpendicular to the line where the blade is located as the first parameter.

17. The printing modification device according to claim 16, wherein the telescopic component further comprises:
a driving unit, coupled to the second end of the extension component to drive the extension component to move in the direction perpendicular to the line where the blade is located, so that the first end of the extension component is in contact with the blade of the printing squeegee.

18. The printing modification device according to claim 16, wherein the displacement sensor comprises:
a displacement conversion circuit, configured to generate an electrical signal related to the displacement of the first end of the extension component in the direction perpendicular to the line where the blade is located;
a signal amplification circuit, configured to perform amplification processing on the electrical signal; and
an analog-to-digital conversion circuit, configured to convert the electrical signal amplified into a digital signal, and calculate the displacement of the first end of the extension component in the direction perpendicular to the line where the blade is located according to the digital signal.

19. The printing modification device according to claim 16, wherein the displacement sensor comprises a first microprocessor, and the first microprocessor is configured to:
generate an electrical signal related to the displacement of the first end of the extension component in the direction perpendicular to the line where the blade is located;
perform amplification processing on the electrical signal; and
convert the electrical signal amplified into a digital signal, and calculate the displacement of the first end of the extension component in the direction perpendicular to the line where the blade is located according to the digital signal.

20. The printing modification device according to claim 13, wherein the blade inspection device further comprises:
a calculation circuit, configured to calculate a difference between the first parameter and a reference parameter; and
an alarm unit, configured to perform an alarm prompt when the difference is greater than a threshold.

* * * * *